United States Patent
Altmann et al.

(10) Patent No.: US 11,304,645 B2
(45) Date of Patent: Apr. 19, 2022

(54) LOCAL RENDERING BASED DETAIL SUBSET PRESENTATION

(71) Applicant: Biosense Webster (Israel) Ltd., Yokneam (IL)

(72) Inventors: Andres Claudio Altmann, Haifa (IL); Vadim Gliner, Haifa (IL); Israel Zilberman, Yokneam (IL); Yair Palti, Herzelia (IL); Remi Bettan, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 393 days.

(21) Appl. No.: 16/653,413

(22) Filed: Oct. 15, 2019

(65) Prior Publication Data

US 2021/0106243 A1 Apr. 15, 2021

(51) Int. Cl.
*A61B 5/339* (2021.01)
*A61B 5/287* (2021.01)
(Continued)

(52) U.S. Cl.
CPC ............ *A61B 5/339* (2021.01); *A61B 5/0538* (2013.01); *A61B 5/287* (2021.01); *G06T 11/60* (2013.01);
(Continued)

(58) Field of Classification Search
CPC . A61B 2576/023; A61B 5/0538; A61B 5/287; A61B 5/339; A61B 5/361; A61B 5/363; A61B 5/6858; A61B 5/7425; A61B 5/743; G06K 2209/051; G06K 9/00671; G06T 11/60; G06T 2210/41; G16H 30/20; G16H 40/63
See application file for complete search history.

(56) References Cited

U.S. PATENT DOCUMENTS

| 5,491,781 A | 2/1996 | Gasperina |
| 2002/0070970 A1 | 6/2002 | Wood et al. |

(Continued)

FOREIGN PATENT DOCUMENTS

| CN | 1628611 A | 6/2005 |
| EP | 1070480 A2 | 1/2001 |
| RU | 2691195 C1 | 6/2019 |

OTHER PUBLICATIONS

European Search Report for corresponding EPA No. 20201807.3 dated Nov. 24, 2020.

*Primary Examiner* — George Manuel
(74) *Attorney, Agent, or Firm* — Volpe Koenig (57) ABSTRACT

Methods, apparatus, and systems for medical procedures are disclosed herein and include receiving a first set of biometric data for a first portion of a body part and determining a first range of values in the first set of biometric data, determining first visual characteristics based on the first range of values and rendering a global view of the first portion of the body part rendered with the first visual characteristics. A second range of values in a second set of biometric data for a second portion of the body part may be determined and the second portion of the body part may be a subset of the first portion of the body part. Second visual characteristics may be determined based on the second range of values and a local view including the second portion of the body part rendered with the second visual characteristics may be rendered.

20 Claims, 9 Drawing Sheets

(51) Int. Cl.
*G16H 30/20* (2018.01)
*G16H 40/63* (2018.01)
*A61B 5/0538* (2021.01)
*G06T 11/60* (2006.01)
*G06V 20/20* (2022.01)

(52) U.S. Cl.
CPC ............. *G06V 20/20* (2022.01); *G16H 30/20* (2018.01); *G16H 40/63* (2018.01); *G06T 2210/41* (2013.01); *G06V 2201/031* (2022.01)

(56) References Cited

U.S. PATENT DOCUMENTS

| | | |
|---|---|---|
| 2002/0103428 A1 | 8/2002 | deCharms |
| 2010/0312094 A1* | 12/2010 | Guttman ................ A61B 34/25 600/411 |
| 2016/0066838 A1 | 3/2016 | DeCharms |
| 2017/0049348 A1 | 2/2017 | Deno |
| 2018/0296108 A1 | 10/2018 | Stewart |

\* cited by examiner

FIG. 6

LOCAL RENDERING BASED DETAIL SUBSET PRESENTATION

FIELD OF INVENTION

The present application provides systems, apparatuses, and methods for improving intra-body visualization.

BACKGROUND

Medical conditions such as cardiac arrhythmia (e.g., atrial fibrillation (AF)) are often diagnosed and treated via intra-body procedures. For example, electrical pulmonary vein isolation (PVI) from the left atrial (LA) body is performed using ablation for treating AF. PVI, and many other minimally invasive catheterizations, require real-time visualization and mapping of an intra-body surface.

Visualization and mapping of intra-body body parts can be performed by mapping propagation of activation waves, fluoroscopies, computerized tomography (CT) and magnetic resonance imaging (MRI), as well as other techniques which may require a greater than desirable amount of time or resources to provide the visualization and mapping.

SUMMARY

Methods, apparatus, and systems for medical procedures are disclosed herein and include receiving a first set of biometric data for a first portion of a body part (e.g., a cardiac chamber), determining a first range of values in the first set of biometric data (e.g., local activation times (LAT), electrical activity, topology, bipolar mappings, dominant frequencies, or impedance values, etc.) and determining first visual characteristics corresponding to the values in the first, set of biometric data based on the first range of values. A second range of values in a second set of biometric data for a second portion of the body part may be determined and the second portion of the body part may be a subset of the first portion of the body part. Further, the second set of biometric data may include a subset of the first set of biometric data. Second visual characteristics corresponding to the values in the second set of biometric data may be determined based on the second range of values. A global view including the first portion of the body part rendered with the first visual characteristics may be rendered and/or provided for display. Additionally, a local view including the second portion of the body part rendered with the second visual characteristics may be rendered and/or provided for display. The local view may be superimposed on the global view at a location on the global view corresponding to the second portion of the body part. The first visual characteristics and the second visual characteristics may be one or more of colors, hues, saturations, patterns, or textures. A problem area may be identified based on the local view.

The first set of biometric data may be sensed by one or more electrodes. The first portion of the body part is one of the entire body part or a subset of the body part. The second portion of the body part is determined based on a user input or via a catheter location.

Additionally, a third range of values in a third set of biometric data for a third portion of the body part may be determined. The third portion of the body part may be a subset of the first portion of the body part. Third visual characteristics corresponding to the values in the third set of biometric data may be determined, based on the third range. A local view including the third portion of the body part may be rendered, or provided for display, with the third visual characteristics. The local view may be superimposed on the global view at a location on the global view corresponding to the third portion of the body part.

First visual characteristics corresponding to the values in the first set of biometric data may be determined based on the first range such that a first subset of the first visual characteristics may be applied to a low end of the first range and the second subset of the first visual characteristic may be applied to a high end of the first range.

BRIEF DESCRIPTION OF THE DRAWINGS

A more detailed understanding can be had from the following description, given by way of example in conjunction with the accompanying drawings wherein.

DETAILED DESCRIPTION

According to embodiments of the disclosed subject matter, a catheter or other insertable device may be inserted into a patient's body and may sense the biometric data of a patient's intra-body body part. For example, elements such as electrodes on an insertable catheter may sense electrical activity data on the surface of a cardiac chamber and provide the electrical activity data to a processor. The processor may generate rendering data that enables a display to render the shape of the cardiac chamber such that the surface of the cardiac chamber shows the electrical activity data using a visual characteristic, as further disclosed herein.

The rendering of a body part may include biometric data for different points of the body part. The biometric data may be rendered using visual characteristics (e.g., colors) shown on the surface of the body part via a display (e.g., a monitor). The biometric data may be visually conveyed using any applicable visual characteristic such as a range or gradient of colors, hues, saturations, patterns, shapes, protrusions (e.g., a 3D protrusion), textures, alphanumeric characters, or the like. To clarify, the shape of a body part, such as a heart, may be rendered via a display, and the surface of the shape may have a visual characteristics (e.g., colors) that convey the values of the biometric data (e.g., local activation time (LAT) values where a first color may represent a first lower range of LAT values and a second color may represent a second higher range of LAT values). The render of the body part may be adjustable such that the viewing angle, zoom amount, position, orientation, and other viewing properties may be adjusted by a user or automatically via a predetermined criteria or dynamically determined criteria.

According to embodiments of the disclosed subject matter, the rendering data may include a global view and a local view. The global view may include the biometric data for a first portion of a body part, which may be the entire body part or the portion of the body part that is rendered on a display at a given time. The global view may show biometric data on the surface of the first portion of the body part using visual characteristics such as colors that indicate different values of the biometric data (e.g., high LAT values may be shown in red verses low LAT values may be shown in purple).

The visual characteristics that indicate different values of the biometric data for the global view may be determined based on the range of values present in the biometric data for first portion of the body part. A wider range of values may result in more values being indicated by the same or similar visual characteristics. For example, the first portion of the body part may be a cardiac chamber with LAT values that range from −500 ms and +500 ms. The visual characteristics used to indicate the LAT values in the global view may be, for example, five colors including red, yellow, green, blue, purple such that red may indicate−500 ms through −301 ms, yellow may indicate−300 ms through −101 ms, green may indicate−100 ms through +99 ms, blue may indicate+100 ms through +299 ms, and purple, may indicate+300 ms through +500 ms.

The local view may be superimposed onto a portion of the global view and may include the biometric data for a second portion of the body part that is contained within the first portion of the body part shown in the global view (e.g., the first portion of the body part may be a cardiac chamber and the second portion of the body part may be a small portion of the cardiac chamber). The local view may show biometric data on the surface of the second portion of the body part using visual characteristics such as colors that indicate different values of the biometric data (e.g., high LAT values may be shown in red vs low LAT values may be shown in purple). The visual characteristics that indicate different values of the biometric data for the local view may be determined based on the range of values present in the biometric data for the second portion of the body part, which may be narrower than the range of values present in the biometric data for the first, larger, portion of the body part. Continuing the example provided above, the local view may be superimposed on a global view. The global view may show a cardiac chamber with LAT values that range from −500 ms through +500 ms indicated by colors and the local view, superimposed onto a portion of the global view over a smaller portion of the cardiac chamber may show LAT values that range from −200 through +150 ms. Accordingly, the visual characteristics used to indicate the LAT values within the local view may be the same five colors as the global view including red, yellow, green, blue, purple such that red may indicate−200 ms through −101 ms, yellow may indicate−100 ms through 0 ms, green may indicate+1 ms through +49 ms, blue may indicate+50 ms through +99 ms, and purple may indicate+100 ms through +150 ms. Notably, the local view may provide a more granular view of the biometric data for the second portion of the body part, by rendering the biometric data using visual characteristics determined by the range of values in the biometric data of the second portion of the body part.

It will be understood that although the disclosure provided herein recites components, attributes, data, renders, and the like, as first, second, third, etc. (referred to as "items"), such designators are provided to distinguish between two or more items and are not necessarily provided to impose an order. As specific examples, a first portion of a body part is distinguished from a second portion of a body part such that the second portion of a body part is a subset of the first portion of a body part. As another example, a first set of biometric data may correspond to a first portion of the body part. The first set of biometric data is distinguished from a second set of biometric data that may correspond to the second portion of the body part.

Figure 1:
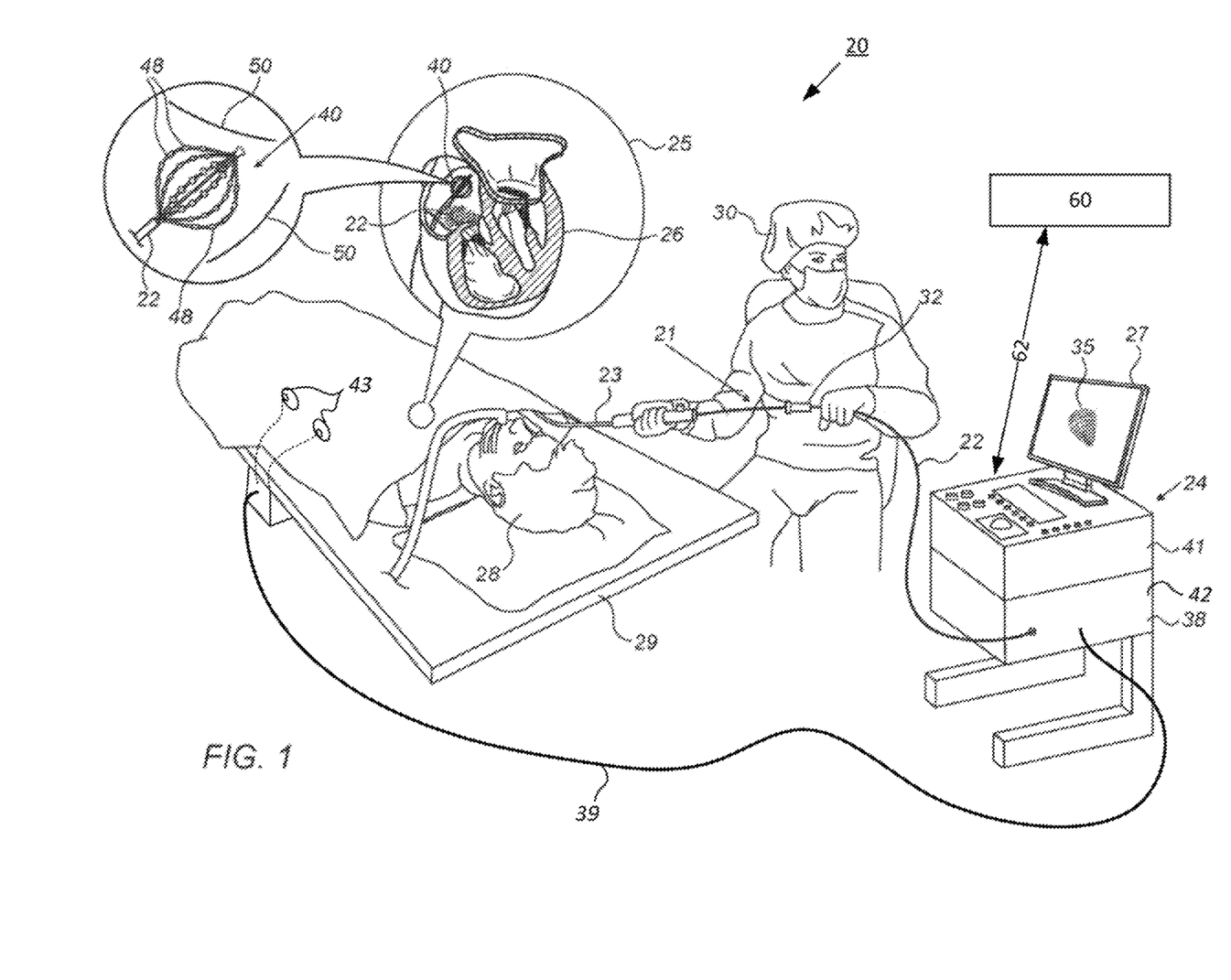
FIG. 1 is a diagram of an exemplary system in which one or more features of the disclosure subject matter can be implemented.

FIG. 1 is a diagram of an exemplary mapping system 20 in which one or more features of the disclosure subject matter can be implemented. Mapping system 20 may include a device, such as a catheter 40, that is configured to obtain biometric data in accordance with an embodiment of the disclosed subject matter. Although catheter 40 is shown to have a basket shape, it will be understood that a catheter of any shape that includes one or more elements (e.g., electrodes) may be used to implement the embodiments disclosed herein. Mapping system 20 includes a probe 21, having a shaft 22 that may be navigated by a medical professional 30 into a body part, such as heart 26, of a patient 28 lying on a table 29. As shown in FIG. 1, medical professional 30 may insert shaft 22 through a sheath 23, while manipulating the distal end of shaft 22 using a manipulator 32 near the proximal end of the catheter and/or deflection from the sheath 23. As shown in an inset 25, catheter 40 may be fitted at the distal end of shaft 22. Catheter 40 may be inserted through sheath 23 in a collapsed state and may be then expanded within heart 26.

According to an embodiment, catheter 40 may be configured to obtain biometric data of a cardiac chamber of heart 26. Inset 45 shows catheter 40 in an enlarged view, inside a cardiac chamber of heart 26. As shown, catheter 40 may include an array of elements (e.g., electrodes 48) coupled onto splines that form the shape of the catheter 40. The elements (e.g., electrodes 48) may be any elements configured to obtain biometric data and may be electrodes, transducers, or one or more other elements.

According to embodiments disclosed herein, biometric data may include one or more of LATS, electrical activity, topology, bipolar mapping, dominant frequency, impedance, or the like. The local activation time may be a point in time of a threshold activity corresponding to a local activation, calculated based on a normalized initial starting point. Electrical activity may be any applicable electrical signals that may be measured based on one or more thresholds and may be sensed and/or augmented based on signal to noise ratios and/or other filters. A topology may correspond to the physical structure of a body part or a portion of a body part and may correspond to changes in the physical structure relative to different parts of the body part or relative to different body parts. A dominant frequency may be a frequency or a range of frequency that is prevalent at a portion of a body part and may be different in different portions of the same body part. For example, the dominant frequency of a pulmonary vein of a heart may be different than the dominant frequency of the right atrium of the same heart. Impedance may be the resistance measurement at a given area of a body part.

As shown in FIG. 1, the probe 21 and catheter 40 may be connected to a console 24. Console 24 may include a processor 41, such as a general-purpose computer, with suitable front end and interface circuits 38 for transmitting and receiving signals to and from catheter 40, as well as for controlling the other components of mapping system 20. In some embodiments, processor 41 may be further configured to receive biometric data and generate rendering data for a global view and local view, based on the biometric data, as further disclosed herein. According to embodiments, the rendering data may be used to provide the medical professional 30 with a rendering of one or more body parts on a display 27, e.g., a body part rendering 35. The display 27 may be located local to the mapping system 20 or may be located remote from one or more other components of mapping system 20. According to an embodiment, the processor may be external to the console 24 and may be located, for example, in the catheter, in an external device, in a mobile device, in a cloud-based device, or may be a standalone processor.

As noted above, processor 41 may include a general-purpose computer, which may be programmed in software to carry out the functions described herein. The software may be downloaded to the general-purpose computer in electronic form, over a network, for example, or it may, alternatively or additionally, be provided and/or stored on non-transitory tangible media, such as magnetic, optical, or electronic memory. The example configuration shown in FIG. 1 may be modified to implement the embodiments disclosed herein. The disclosed embodiments may similarly be applied using other system components and settings. Additionally, mapping system 20 may include additional components, such as elements for sensing biometric patient data, wired or wireless connectors, processing and display devices, or the like.

According to an embodiment, a display connected to a processor (e.g., processor 41) may be located at a remote location such as a separate hospital or in separate healthcare provider networks. Additionally, the mapping system 20 may be part of a surgical system that is configured to obtain anatomical and electrical measurements of a patient's organ, such as a heart, and performing a cardiac ablation procedure. An example of such a surgical system is the Carto® system sold by Biosense Webster.

The mapping system 20 may also, and optionally, obtain biometric data such as anatomical measurements of the patient's heart using ultrasound, computed tomography (CT), magnetic resonance imaging (MRI) or other medical imaging techniques known in the art. The mapping system 20 may obtain electrical measurements using catheters, electrocardiograms (EKGs) or other sensors that measure electrical properties of the heart. The biometric data including anatomical and electrical measurements may then be stored in a local memory 42 of the mapping system 20, as shown in FIG. 1. The biometric data may be transmitted to the processor 41 from the memory 42. Alternatively, or in addition, the biometric data may be transmitted to a server 60, which may be local or remote, using a network 62.

Network 62 may be any network or system generally known in the art such as an intranet, a local area network (LAN), a wide area network (WAN), a metropolitan area network (MAN), a direct connection or series of connections, a cellular telephone network, or any other network or medium capable of facilitating communication between the mapping system 20 and the server 60. The network 62 may be wired, wireless or a combination thereof. Wired connections may be implemented using Ethernet, Universal Serial Bus (USB), RJ-11 or any other wired connection generally known in the art. Wireless connections may be implemented using WiMAX, and Bluetooth, infrared, cellular networks, satellite or any other wireless connection methodology generally known in the art. Additionally, several networks may work alone or in communication with each other to facilitate communication in the network 62.

In some instances, the server 60 may be implemented as a physical server. In other instances, server 60 may be implemented as a virtual server a public cloud computing provider (e.g., Amazon Web Services (AWS)®).

Control console 24 may be connected, by a cable 39, to body surface electrodes 43, which may include adhesive skin patches that are affixed to the patient 28. The processor, in conjunction with a current tracking module, may determine position coordinates of the catheter 40 inside the body part (e.g., heart 26) of a patient. The position coordinates may be based on impedances or electromagnetic fields measured between the electrodes 43 and the electrodes 48 or other electromagnetic components of the catheter 40.

Processor 41 may comprise real-time noise reduction circuitry typically configured as a field programmable gate array (FPGA), followed by an analog-to-digital (A/D) ECG (electrocardiograph) or EMG (electromyogram) signal conversion integrated circuit. The processor 41 may pass the signal from an A/D ECG or EMG circuit to another processor and/or can be programmed to perform one or more functions disclosed herein.

Control console 24 may also include an input/output (I/O) communications interface that enables the control console to transfer signals from, and/or transfer signals to electrodes 48 and electrodes 43. Based on signals received from electrodes 48 and/or electrodes 43, processor 41 may generate rendering data that enables a display, such as display 27 to render a body part, such as a body part rendering 35.

During a procedure, processor 41 may facilitate the presentation of a body part rendering 35, including a global view and a local view, to medical professional 30 on a display 27, and store data representing the body part rendering 35 in a memory 42. Memory 42 may comprise any suitable volatile and/or non-volatile memory, such as random-access memory or a hard disk drive. In some embodiments, medical professional 30 may be able to manipulate a body part rendering 35 using one or more input devices such as a touch pad, a mouse, a keyboard, a gesture recognition apparatus, or the like. In alternative embodiments, display 27 may include a touchscreen that can be configured to accept inputs from medical professional 30, in addition to presenting a body part rendering 35, including a global view and a local view.

Figure 2:
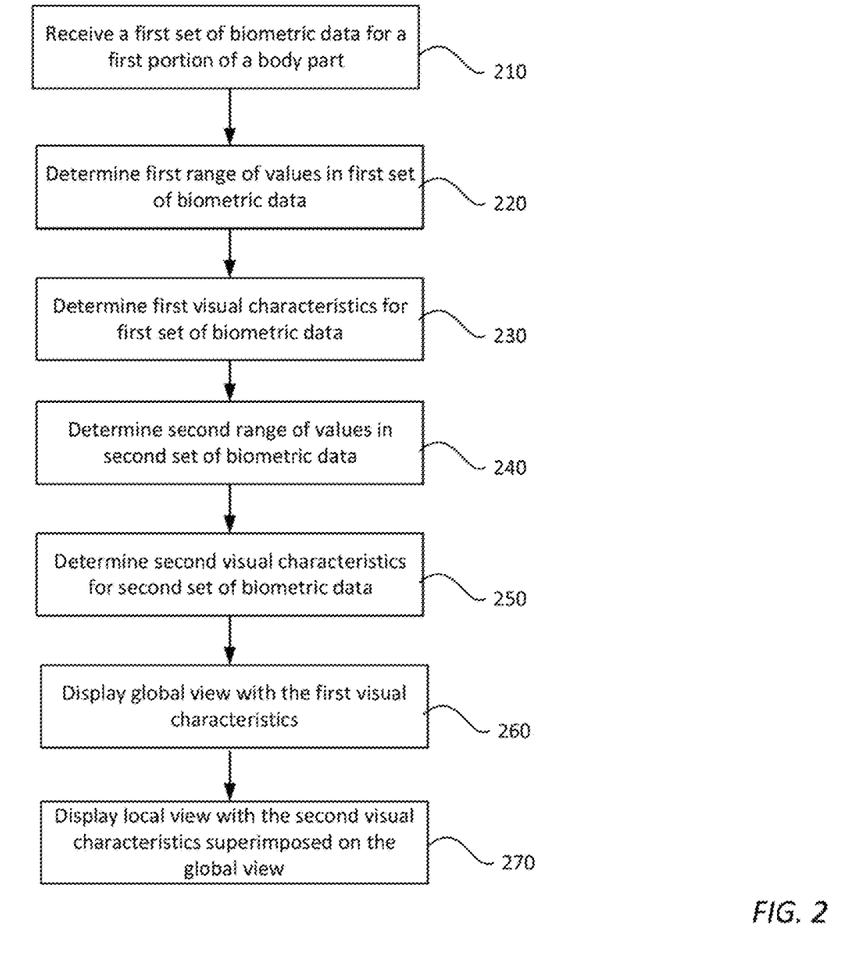
FIG. 2 is a flowchart for displaying a global view and a local view.

FIG. 2 shows a process 200 for displaying a global view and a local view, as disclosed herein. At step 210 of the process 200, a first set of biometric data for a first portion of a body part may be received. The body part may be any body part or part of a body part in a patient's body such as an organ, muscle, tissue, ligament, or the like. For example, the body part may be a heart and the first portion of the body part may be a chamber in the heart or a part of a chamber in the heart. The first set of biometric data may be sensed by a catheter, such as catheter 40 of FIG. 1. The catheter may include one or more elements, such as electrodes or transducers, that may be configured to sense the first set of biometric data. The catheter may be inserted into a patient's body through a natural orifice or through an incision created at a location on the patient's body. The catheter may traverse the surface of the body part (e.g., heart) and may collect the first set of biometric data during time intervals when the catheter rests at various points on the surface of the body part. As an example, the catheter may rest on 500 different points on the surface of a heart and collect LAT values over 2.5 second intervals during which intervals the catheter rest on each of the 500 different points on the surface of the heart. The first set of biometric data may be stored in a memory, such as memory 42 of FIG. 1.

The first set of biometric data may be received by a processor, such as processor 41 of FIG. 1. The first set of biometric data may be received by the processor over a wired or wireless connection between the catheter, such as catheter 40 of FIG. 1 and the processor, such as processor 41. The first set of biometric data may be received by the processor as each data point is sensed by the catheter or the catheter may sense the entire first set of biometric data and provide it to the processor once the entire set is sensed.

At step 220 of the process illustrated in FIG. 2, the first range of values for the first set of biometric data may be determined. The first range of values may be determined by a processor such as processor 41 of FIG. 1. The first range of values may be determined based on the maximum and minimum biometric data values within the first set of biometric data. For example, if the first set of biometric data includes LAT values that range from a lowest LAT value of −500 ms to a highest. LAT value of +500 ms, then the first range may be −500 ms to +500 ms. The first range of values may be a filtered set of values where the filter may be, for example, a high pass filter, a low pass filter, an averaging filter, a filter that removes outlier values, or the like. For example, a filter may be applied such that 5% of the lowest values within the first set of biometric data and 5% of the highest values within the first set of biometric data are removed from the first set of biometric data. The first range of values may be stored in a memory, such as memory 42 of FIG. 1.

At step 230 of the process illustrated in FIG. 2, first visual characteristics corresponding to the values in the first set of biometric data may be determined based on the first range of values. The first visual characteristics may be any visual characteristics that visually convey the different values in the first set of biometric data and may be one or more of colors, hues, saturations, patterns, shapes, protrusions, textures, or alphanumeric characters. For example, the visual characteristics may be different colors that correspond to respective different ranges of LAT values. The values in the first set of biometric data may be segmented and a different visual characteristic from the first visual characteristics may be assigned to each segment. The number of values represented by each visual characteristic may be determined based on how wide or narrow the first range of values is. A wide range of values may result in segments that include a larger number of values in each segment and a narrow range of values may result in segments that include a smaller number of values in each segment. As described in the example provided herein, if the values in the first set of biometric data range from −500 ms to +500 ms, then the visual characteristics used to indicate the LAT values may be, for example, five colors including red, yellow, green, blue, purple such that red may indicate a segment of −500 ms through −301 ms, yellow may indicate a segment of −300 ms through −101 ms, green may indicate a segment of −100 ms through +99 ms, blue may indicate a segment of +100 ms through +299 ms, and purple may indicate a segment of +300 ms through +500 ms.

Notably, the first visual characteristics for the first set of biometric data which corresponds to a first portion of a body part (e.g., the whole body part or a portion of the body part) may be used to display a global view of the body part such that the first range of values may be larger than a second range of values used to display a local view of a smaller subset of the body part (i.e., second portion of the body part), as further described herein. The first range of values, and the corresponding first visual characteristics, may be large such that granular details of the biometric data corresponding to the smaller subsets of the body part are not discernable when viewing the first visual characteristic in the global view, as further described herein.

Figure 5A:
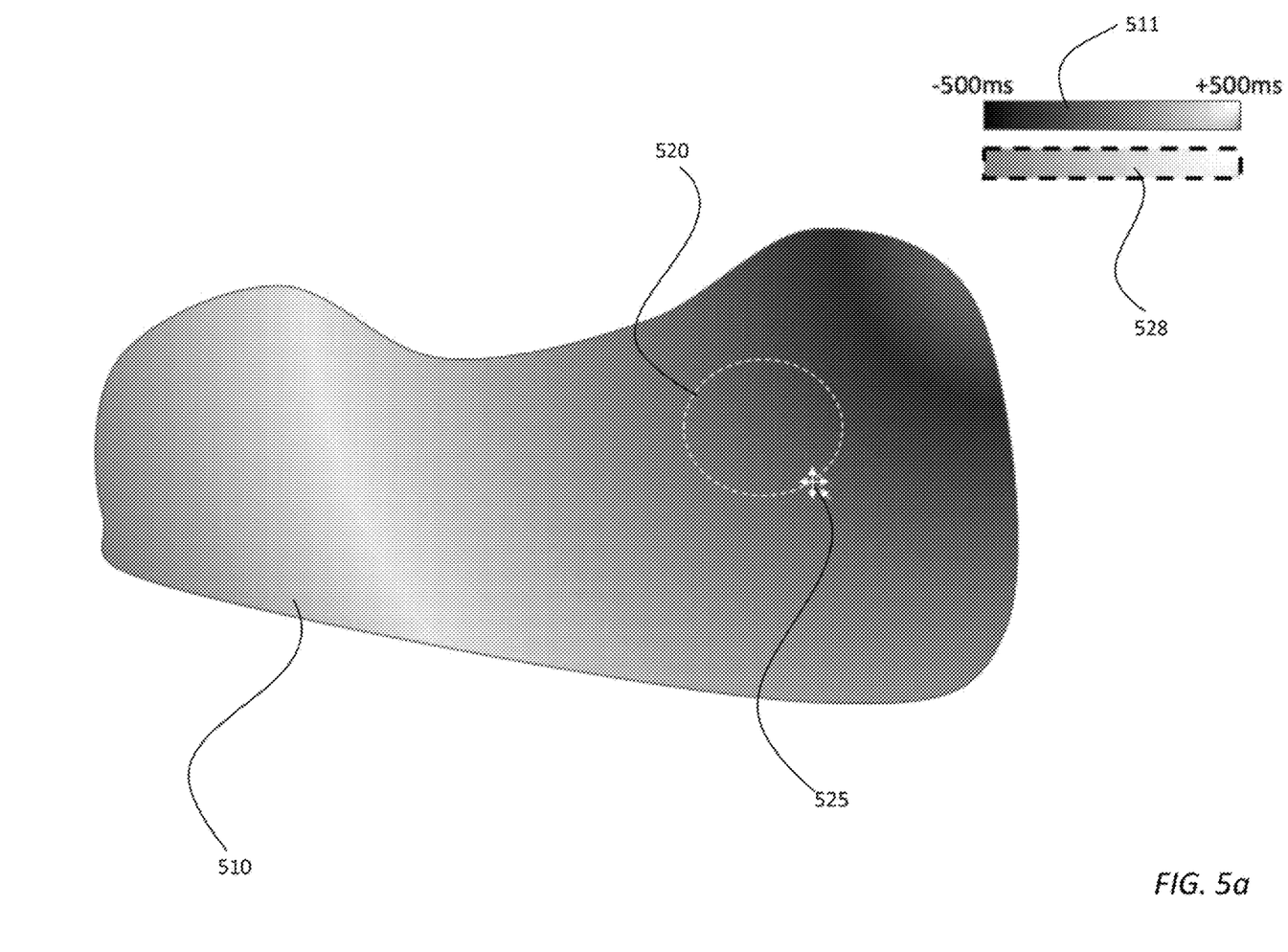
FIG. 5A is a diagram of a first portion of a body part rendered as a global view and selection of a local view.
Figure 5B:
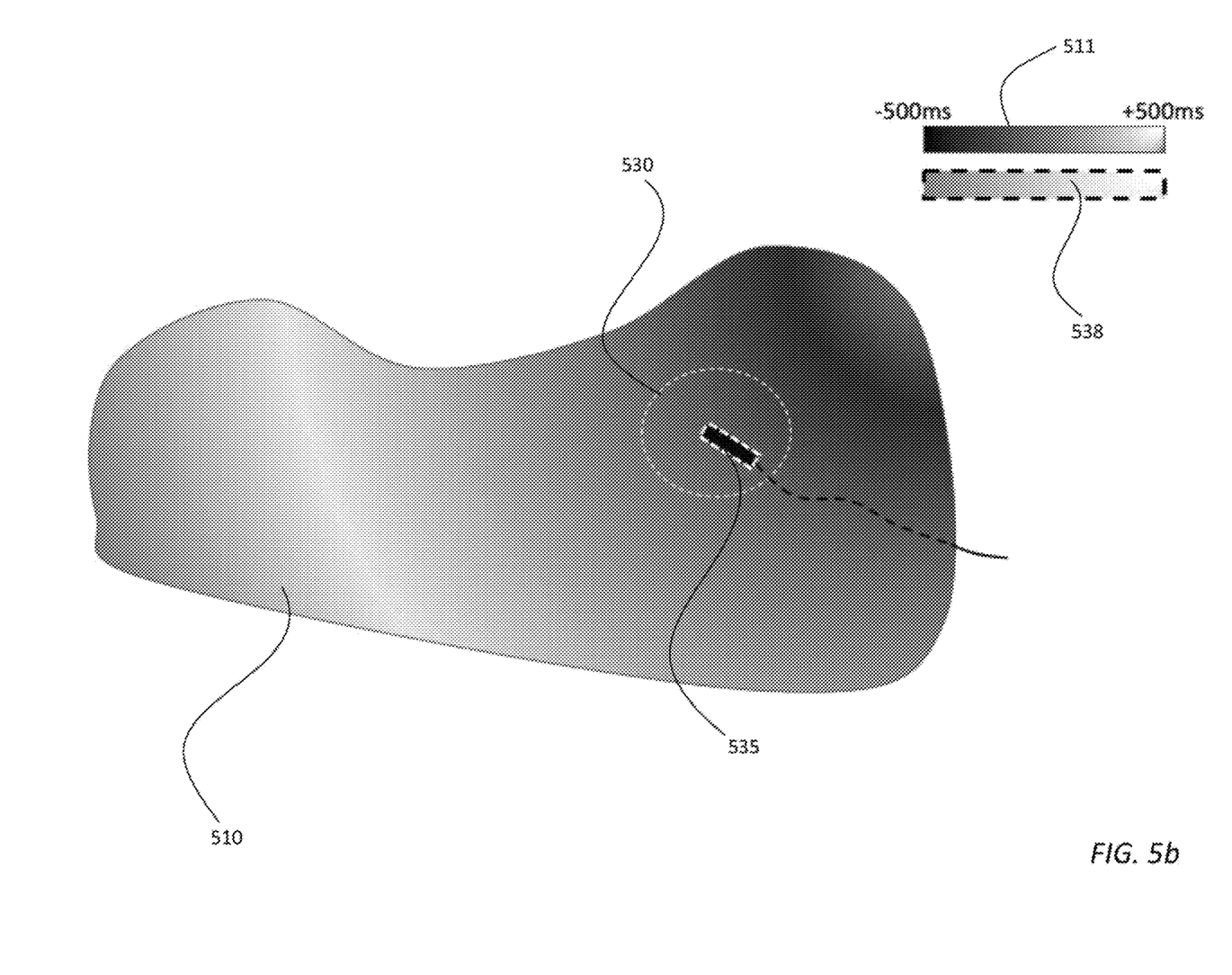
FIG. 5B is a diagram of a first portion of a body part rendered as a global view and catheter location-based selection of a global view.

A second portion of the body part may be determined. The second portion of the body part may be a subset of the first portion of the body part such that the second portion of the body part corresponds to an area within the first portion of the body part. The second portion of the body part may be determined based on user input, as illustrated in FIG. 5A, as further descried herein. Alternatively, the second portion of the body part may be determined based on the location of a catheter, such as the catheter that is used to sense the first set of biometric data at step 210 of the process illustrated in FIG. 2, as illustrated in FIG. 5B, as further described herein.

At step 240 of the process illustrated in FIG. 2, the second range of values in a second set of biometric data may be determined. The second set of biometric data may correspond to the second portion of the body part that is a subset of the first portion of the body part and may include the biometric data values from the first set of biometric data that correspond to the area occupied by the second portion of the body part. Additionally, the second set of biometric data may include additional biometric data values sensed by a catheter. The additional biometric data values may be sensed by the catheter upon the determination of the second portion of the body part.

The second range of values may be determined by a processor such as processor 41 of FIG. 1. The second range of values may be determined based on the maximum and minimum biometric data values within the second set of biometric data. For example, if the second set of biometric data includes LAT values that range from a lowest LAT value of −200 ms to a highest LAT value of +150 ms, then the first range may be −200 ms to +150 ms. The second range of values may be a filtered set of values as described herein for the disclosure related to the first range of values.

At step 250 of the process illustrated in FIG. 2, second visual characteristics corresponding to the values in the second set of biometric data may be determined based on the second range of values. The second visual characteristics may be any visual characteristics that visually convey the different values in the second set of biometric data and may be one or more of colors, hues, saturations, patterns, shapes, protrusions, textures, or alphanumeric characters. The second visual characteristics may be the same as or a subset of the visual characteristics determined based on the first range of values for the first subset of biometric data. As an example of the second visual characteristics, the second visual characteristics may be different colors that correspond to respective different ranges of LAT values. The values in the second set of biometric data may be segmented and a different visual characteristic from the second visual characteristics may be assigned to each segment. The number of values represented by each visual characteristic may be determined based on how wide or narrow the second range of values is. As described in the example provided herein, if the values in the second set of biometric data range from −200 ms to +150 ms, then the second visual characteristics used to indicate the LAT values may be the same five colors as the first visual characteristics, including red, yellow, green, blue, purple such that red may indicate a segment of −200 ms through −101 ms, yellow may indicate−100 ms through 0 ms, green may indicate+1 ms through +49 ms, blue may indicate 50 ms through 99 ms, and purple may indicate+100 ms through +150 ms.

Notably, the second visual characteristics for the second set of biometric data which corresponds to the second portion of a body part (i.e., a subset of the first portion of the body part) may be used to display a local view of the second portion of the body part such that the second range of values may be smaller than the first range of values used to display the global view of the larger first portion of the body part, as further described herein. The second range of values, and the corresponding second visual characteristics, may be small such that granular details of the biometric data corresponding to the smaller second portion of the body part are discernable when viewing the second visual characteristic in the local view, as further described herein.

Figure 3:
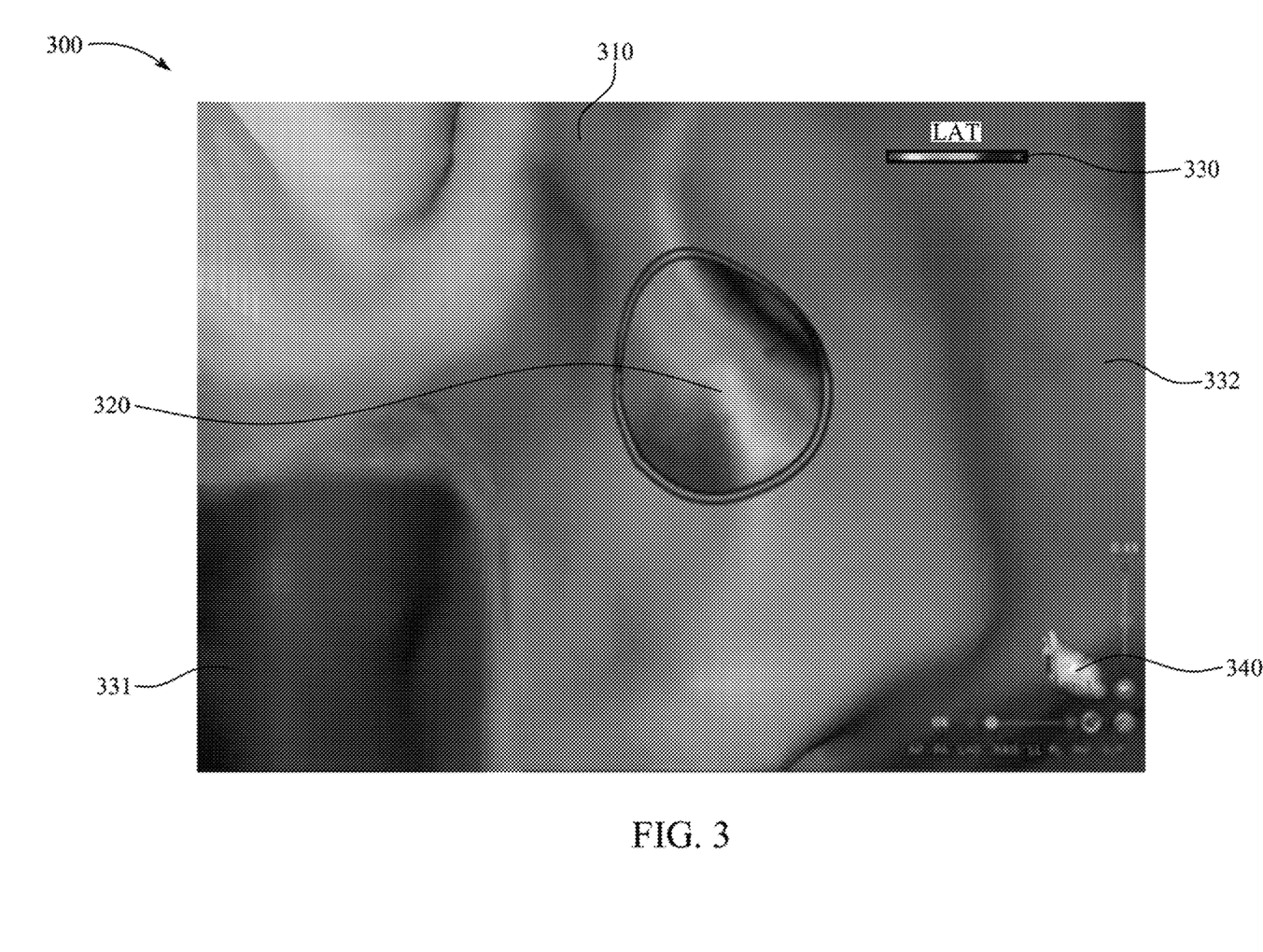
FIG. 3 is an image of a local view superimposed on a global view.

At step 260 of the process illustrated in FIG. 2, a global view with the first visual characteristics may be displayed. The global view may include a render of the first portion of the body part such that the surface of the first portion of the body part is rendered using the first visual characteristics. Accordingly, the global view may show the first portion of the body part with the first visual characteristics that visually indicate the values of the first set of biometric data via the first visual characteristics. FIG. 3 is an image 300 of a display that shows a global view 310 of a first portion of a cardiac chamber. As shown in FIG. 3, the global view 310 is a render of a first portion of the cardiac chamber and the surface of the render of the first portion of the cardiac chamber is represented by light grey to dark grey visual characteristics such as a light grey portion 332 and dark grey portion 331. The light grey portions of the surface correspond to the lower LAT values as indicated in legend 330 and the dark grey portions of the surface corresponds to higher LAT values, as also indicated in the legend 330. Notably, the global view 310 of the first portion of the cardiac chamber includes visual characteristics that correspond to large segments of ranges of LAT values when compared to the local view 320 corresponding to legend 321, as further disclosed herein.

FIG. 3 also shows a reference orientation 340 that indicates the orientation of the cardiac chamber that is currently displayed via the global view 310. The orientation of the global view 310 may be changed and the reference orientation 340 may adjust based on the change. For example, a user may provide an input by pressing on a mouse button and moving the mouse to rotate the global view 310 such that a different area of the cardiac chamber is displayed. According to this example, the reference orientation 340 may a change to reflect the change in orientation of the cardiac chamber being displayed.

At step 260 of the process illustrated in FIG. 2, a local view with the second visual characteristics may be displayed. The local view may be superimposed on the global view and may include a render of the second portion of the body part such that the surface of the second portion of the body part is rendered using the second visual characteristics. The second portion of the body part may be a subset of the first portion of the body part, as disclosed herein. Accordingly, the local view may show the second, smaller, portion of the body part with the second visual characteristics that visually indicate the values of the second set of biometric data via the second visual characteristics. FIG. 3 shows a local view 320 of a second portion of a cardiac chamber superimposed on the global view 310. As shown in FIG. 3, the local view 320 includes a render of a second portion of the cardiac chamber and the surface of the render of the second portion of the cardiac chamber is represented by a more granular range of light grey to dark grey visual characteristics than the smoother range of light grey to dark grey visual characteristics of the global view 310. The light grey portions of the surface correspond to the lower LAT values within the subset of LAT values that correspond to the smaller area occupied by the second portion of the cardiac chamber. Similarly, the dark grey portions of the surface within the local view 320 corresponds to higher LAT values within the subset of LAT values that correspond to the smaller area occupied by the second portion of the cardiac chamber. Notably, the local view 320 of the second, smaller, portion of the cardiac chamber includes visual characteristics that correspond to smaller segments of LAT values when compared to the global view 310.

The global view, such as global view 310 of FIG. 3, and the local view, such as local view 320, may be generated by a processor, such as processor 41 of FIG. 1 and may be provided to a display, such as display 27. The processor may update the global view and/or the local view based on updated first set of biometric data or second set of biometric data and the global view and local view rendered on a display may be updated accordingly. The values of the updated first set of biometric data or second set of biometric data may be provided based on additional biometric data sensed by a catheter, such as catheter 40.

Figure 4A:
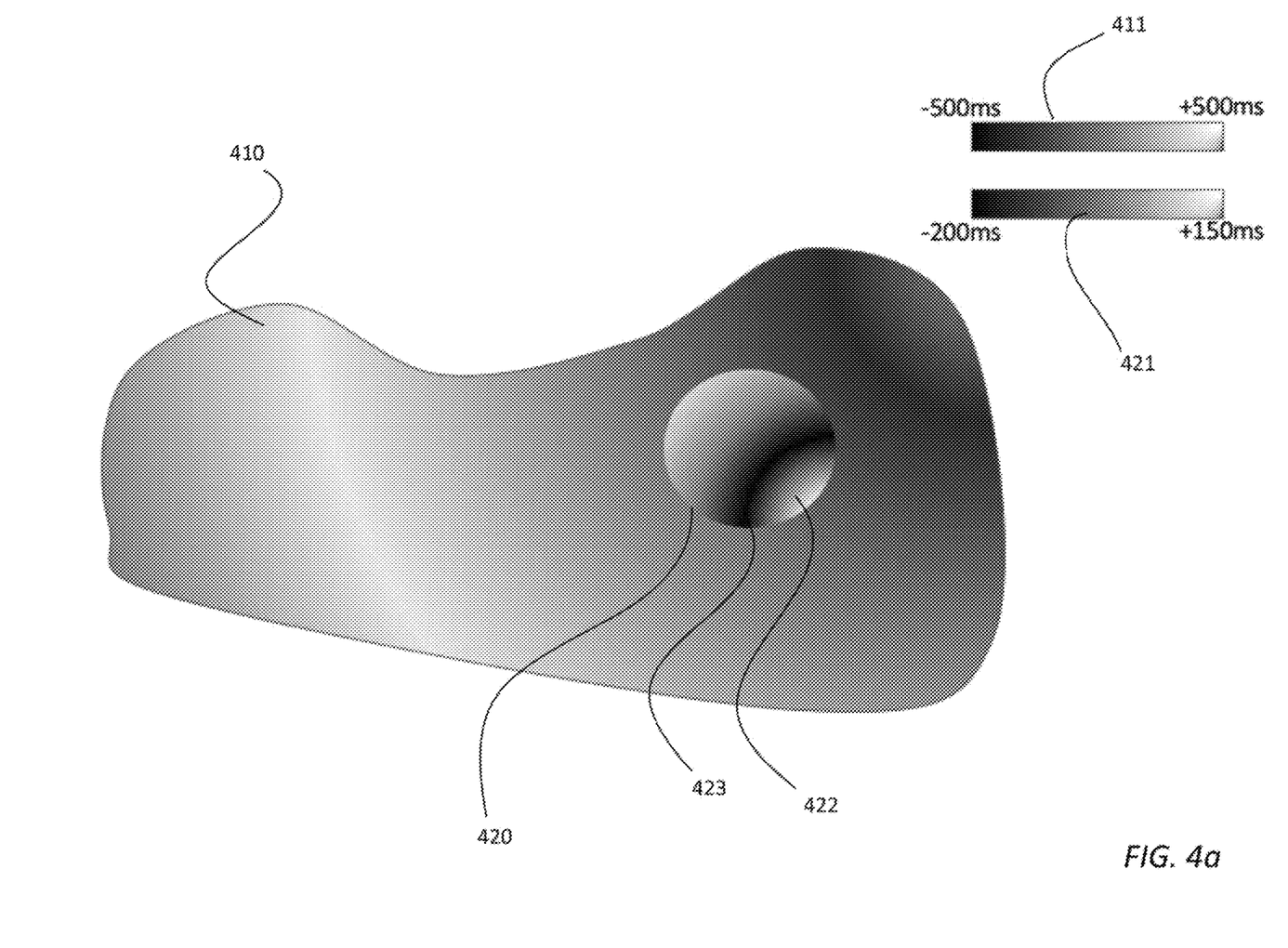
FIG. 4A is a diagram of a first portion of a body part rendered as a global view and local view superimposed on the global view.

FIG. 4A shows a simplified illustration of a global view 410 and local view 420, in accordance with embodiments disclosed herein. As shown in FIG. 4A, global view 410 includes a render of a first portion of a body part using first visual characteristics that include gradients of grey that range from light grey to dark grey. The first visual characteristics of the global view 410 correspond to a wide range of LAT values that range from −500 ms to +500 ms as shown in global view legend 411. Notably, the global view 410 of the first, larger, portion of the body part is rendered using first visual characteristics that correspond to larger segments of LAT values (i.e., segments allocated based on the range of LAT values from −500 ms to +500 ms) when compared to the local view 420. The local view 420, which corresponds to a smaller second portion of the body part, that is a subset of the first portion of the body part, includes a render of the smaller second portion of the body part using second visual characteristics that include gradients of grey that range from light grey to dark grey. The second visual characteristics of the local view 420 correspond to a narrower range of LAT values that range from −200 ms to +150 ms as shown in local view legend 421. Notably, the local view 420 of the second, smaller, portion of the body part is rendered using second visual characteristics that correspond to smaller segments of LAT values (i.e., segments allocated based on the range of LAT values from −200 ms to +150 ms) when compared to the global view 410. As shown in the local view 420, the dark grey visual characteristic 423 and light grey visual characteristic 422 correspond to granular differences in biometric data, within the area occupied by the second portion of the body part, such that the granular differences would not be visually shown in the global view 410.

Figure 4B:
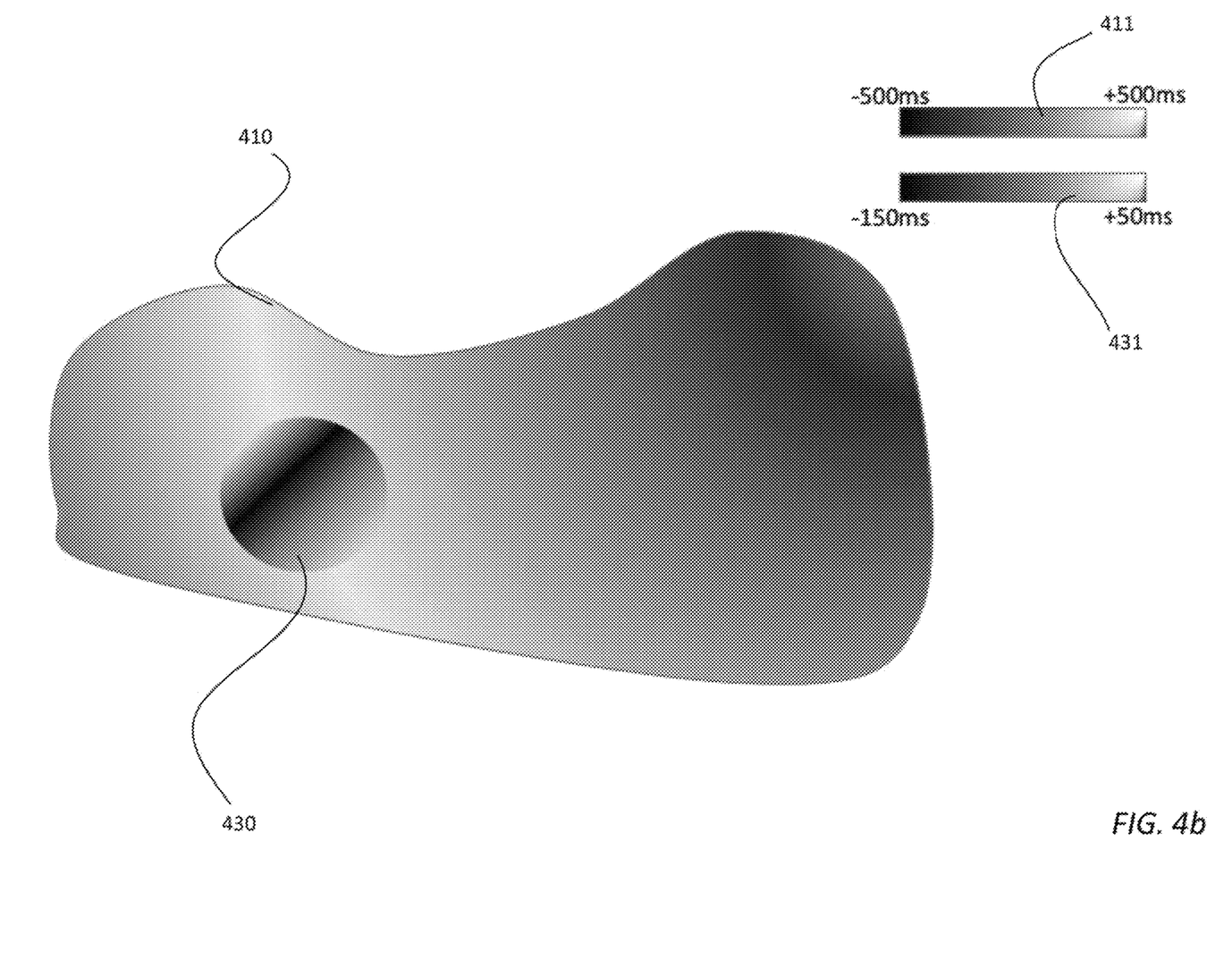
FIG. 4B is another diagram of the first portion of a body part of FIG. 4A rendered as a global view and different local view superimposed on the global view.

According to an embodiment of the disclosed subject matter, as shown in FIG. 4B, a different local view 430 may be shown superimposed on the same global view 410 as shown in FIG. 4A. The local view 430 may correspond to a smaller body part that is a subset of the first body part that corresponds to the global view 410. The local view 430 may be rendered in response to receiving a selection of the smaller body part that corresponds to the location of the local view 430. The selection of the smaller body part may be provided by a user, as shown in FIG. 5A, as further disclosed herein. Alternatively, the local view 430 may be rendered in response to the movement of a catheter to the area that corresponds to the location of the local view 430, as shown in FIG. 5B and further disclosed herein.

The local view 430 of FIG. 4B may include visual characteristics that are determined based on the range of biometric data values specific to the second portion of the body part associated with the area of the local view 430. Accordingly, the range of values associated with the local view 430, as shown via local view legend 431 may be different than the local view legend 421 of the local view 420 if FIG. 4A.

Figure 4C:
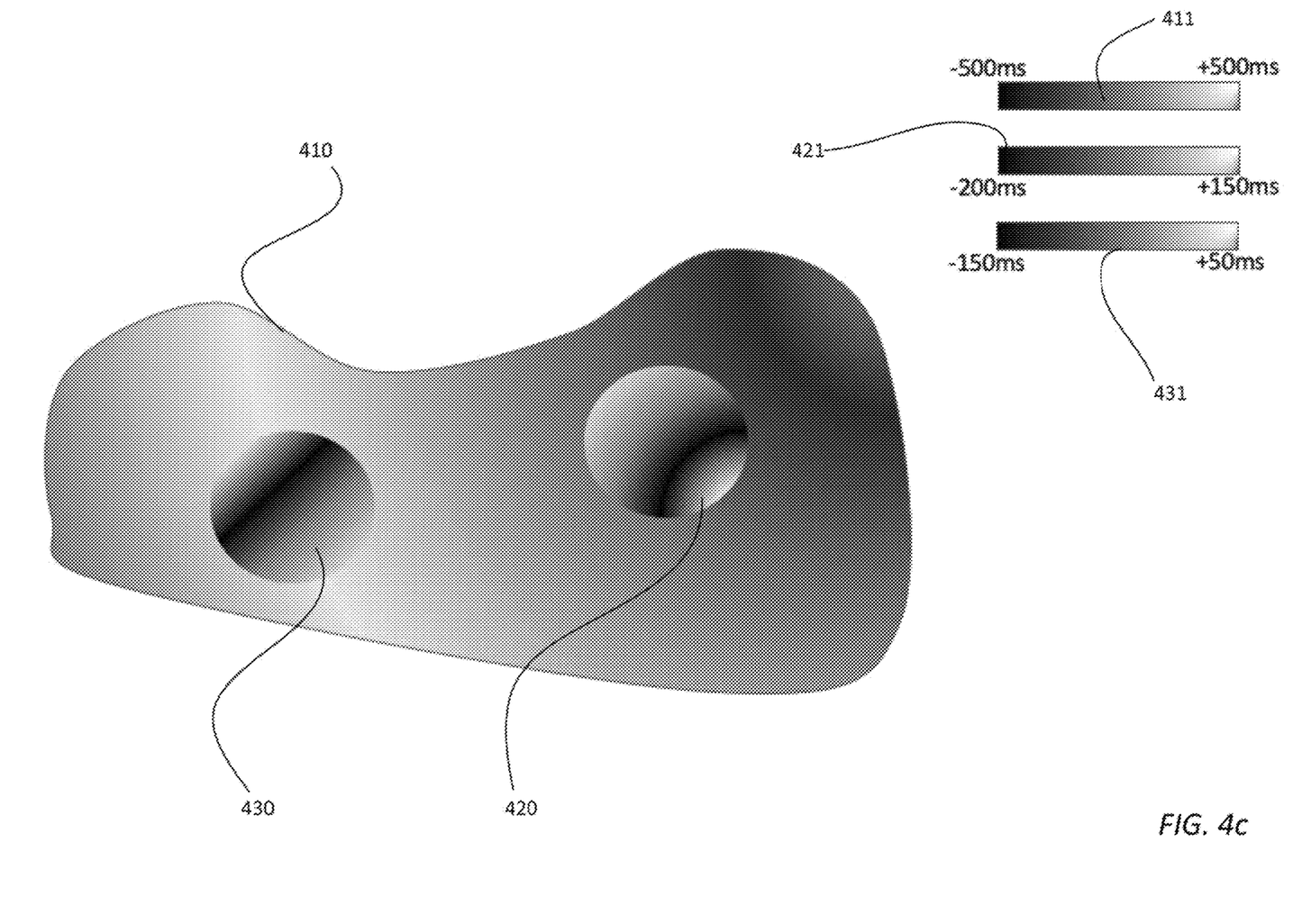
FIG. 4C is another diagram of the first portion of a body part of FIG. 4A rendered as a global view and two local views superimposed on the global view.

According to an embodiment of the disclosed subject matter, as shown in FIG. 4C, two or more local views, such as local view 420 and local view 430 may be displayed simultaneously. The number of local views to be displayed simultaneously may be determined by a system configuration, by user input, system resources, predetermined criteria, dynamically determined criteria, or the like. As shown in FIG. 4C, local views 420 and 430 may be superimposed onto the global view 410 simultaneously. Global view 410 may be rendered using visual characteristics that are determined based on the widest range of biometric data, as shown in global view legend 411 (i.e., LAT values ranging from −500 ms to +500 ms) based on the wide range of biometric data corresponding to the entire first portion of the body part that the global view 410 corresponds to. Local view 420 may be rendered using visual characteristics that are determined based on a narrower range of biometric data, as shown in local view legend 421 (i.e., LAT values ranging from −200 ms to +150 ms) based on the narrower range of biometric data, when compared to the wide range of biometric data corresponding to global view 410, corresponding to the second portion of the body part that local view 420 corresponds to. Similarly, local view 430 may be rendered using visual characteristics that are determined based on the narrowest range of biometric data, as shown in local view legend 431 (i.e., LAT values ranging from −150 ms to +50 ms) based on the narrowest range of biometric data, when compared to the wide range of biometric data corresponding to global view 410 and the range of biometric data corresponding to local view 420, corresponding to the third portion of the body part that local view 430 corresponds to.

FIG. 5A shows a simplified illustration of a user selection 520 of a second portion of a body part. As shown in FIG. 5A, a global view 510 may be rendered and may convey biometric data information using visual characteristics determined based on the range of values of the biometric data associated with a first portion of a body part, the range shown via global view legend 511. A user may provide an input for the selection of a second, smaller, portion of a body part that is a subset of the first portion of the body part that corresponds to the global view 510. The user input may be provided any applicable means such as by a physical input device (e.g., mouse, keyboard, a touch screen, stylus, etc.), a voice command, a gesture, or the like. FIG. 5A shows an example of a circular user selection that may be provided by a user depressing a mouse button when cursor 525 is towards a top portion of the circle that makes up the user selection 520 and dragging the mouse down towards the position of the cursor 525 shown in FIG. 5A. The user may release the mouse button and the user selection 520 may be treated as an input that determines the second body portion corresponding to the user selection 520. The second body portion corresponding to the user selection 520 may be applied, at step 240 of the process disclosed in FIG. 2, to determine a second range of values in a second set of biometric data corresponding to the second portion of the body part based on the user selection 520. The range of biometric data corresponding to the second portion of the body part may be shown in local view legend 528 which may change based on the area selected by the user.

FIG. 5B shows a simplified illustration of a determination of a second portion of a body part based on the location of catheter 535. As shown in FIG. 5B, a global view 510 may be rendered and may convey biometric data information using visual characteristics determined based on the range of values of the biometric data associated with a first portion of a body part, the range shown via global view legend 511. The location of a catheter 535 may be determined based on visual cues, electromagnetic transmissions that facilitate communication with a location track pad or electrodes 43 of FIG. 1. The location of the catheter 535 may result in a determination of the second portion of the body part corresponding to the selected area 530. The second portion of the body part corresponding to the selected area 530 may be applied, at step 240 of the process disclosed in FIG. 2, to determine a second range of values in a second set of biometric data corresponding to the second body portion based on the selected area 530. Notably, the location of the selected area 530 may change based on movement of the catheter 535. The range of biometric data corresponding to the second portion of the body part may be shown in local view legend 538 which may change based on the location of the catheter 535.

Figure 6:
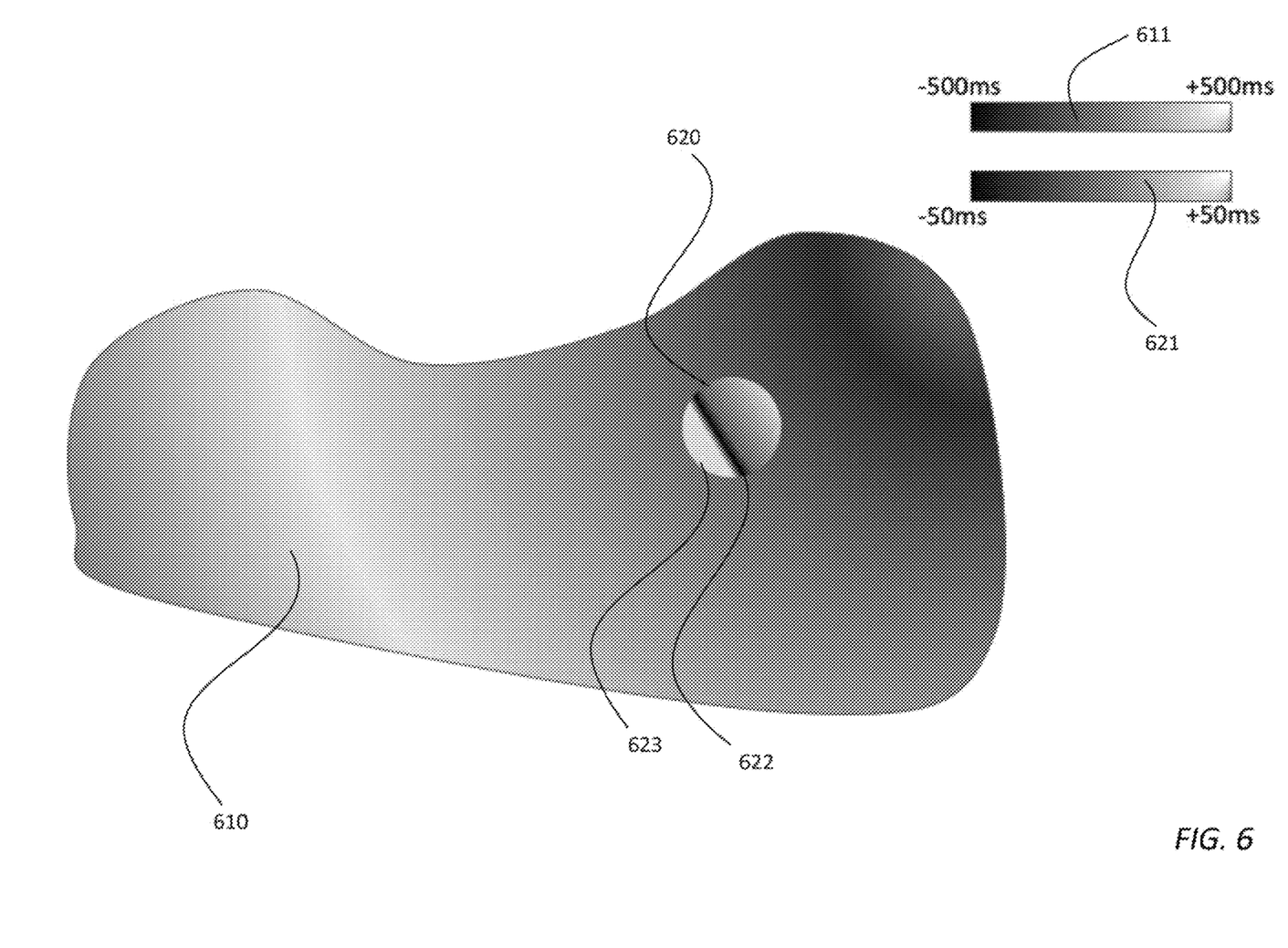
FIG. 6 is a diagram of a first portion of a body part rendered as a global view and a local view including a problem area.

According to an embodiment of the disclosed subject matter, a local area may enable identification of problem areas such as scars, dead tissue, overly active tissue, electric signal rotors, or the like. FIG. 6 shows a global view 610 that may be rendered and may convey biometric data information using visual characteristics determined based on the range of values of the biometric data associated with a first portion of a body part, the range shown via global view legend 611. A local view 620 may be superimposed over the global view 610 and the local view 620 may correspond to a second portion of the body part for which the biometric data exhibits a problem condition. Such a second portion of the body part may be identified based on an analysis of the biometric data corresponding to the entire first portion of the body part. The analysis may include evaluating changes in biometric data over an area, such as the surface area of a heart. Alternatively, or in addition, the analysis may include applying a pre-determined filter or machine learning algorithm to the biometric data of the first portion of the body part corresponding to the global view 610.

The second portion of the body part that corresponds to the local view 620 may be automatically identified based on the analysis of the biometric data corresponding to the entire first portion of the body part. Based on the automatic identification, the local view 620 may be selected. The analysis may be conducted based on stored algorithms (e.g., in memory 42 of FIG. 1) that are generated based on previous or known identifications of problem areas.

As noted, a problem area may be one or more scars, dead tissue, overly active tissue, electric signal rotors, or the like. As an example, a scar may be identified by abnormal LAT values within a given area of a body part. The abnormal LAT values may, for example, be a sharp change in LAT values such as between LAT values 623 and 622 which correspond to the local view legend 621. The scar may not be large enough such that the associated abnormal LAT values are distinguishable within the segments shown by visual characteristics of the global view 610 across the range indicated by global view legend 611. However, the system, such as mapping system 20 of FIG. 1, may gather higher resolution LAT values and determine that a scar is present at a given second location of a body part, based on an analysis of the LAT values. Based upon such a determination, the local view 620 may be provided and may be rendered with visual characteristics selected based on narrow segments of values from a narrow second set of biometric data.

Another problem area may be a live tissue area between a scar. Such an area may be identified based on biometric data that includes bipolar amplitudes. The bipolar amplitudes for an entire first portion of a body part may span wide range such that a live tissue area between a scar may not be visible on a global view. Similarly, another problem area may be a rotor signal, such as an electrical signal at a portion of a chamber that exhibits a circular pattern. A rotor signal is often indicative of the source of AFib. The biometric data of a first portion of a body part may include electrical activity which may be analyzed to detect a rotor signal. The electrical activity of the entire first portion of the body part may span a wide range such that the rotor signal may not be visible on a global view.

A local view, such as local view 620 of FIG. 6 may be provided over a global view 610 and may correspond to the area of the first portion of a body part that exhibits live tissue within scar tissue. The local view may correspond to a second, smaller, portion of the body part and may be a subset of the entire first portion of the body part rendered in the global view 610. The local view 620 may be rendered and may convey biometric data (e.g., the bipolar data to identify live tissue in a scar or the rotor signal based on electrical activity data) using visual characteristics determined based on the range of values of the biometric data associated with the second, smaller, portion of a body part, as disclosed herein.

Any of the functions and methods described herein can be implemented in a general-purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer-readable media). The results of such processing can be maskworks that are then used in a semiconductor manufacturing process to manufacture a processor which implements features of the disclosure.

Any of the functions and methods described herein can be implemented in a computer program, software, or firmware incorporated in a non-transitory computer-readable storage medium for execution by a general purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

The invention claimed is:

1. A method comprising:
   receiving a first set of biometric data for a first portion of a body part;
   determining a first range of values in the first set of biometric data;
   determining first visual characteristics corresponding to the first range of values;
   determining a second range of values in a second set of biometric data for a second portion of the body part, the second portion of the body part being a subset of the first portion of the body part and the second set of biometric data comprising a subset of the first set of biometric data;
   determining second visual characteristics corresponding to the second range of values;
   providing, for display, a first view comprising the first portion of the body part rendered with the first visual characteristics; and
   providing, for display, a second view comprising the second portion of the body part rendered with the second visual characteristics, the second view superimposed on the first view at a location on the first view corresponding to the second portion of the body part.

2. The method of claim 1, wherein the first visual characteristics and the second visual characteristics are one or more of colors, hues, saturations, protrusions, patterns, textures, and alphanumeric characters.

3. The method of claim 1, wherein the body part comprises a cardiac chamber.

4. The method of claim 1, wherein the first set of biometric data is one of a local activation time (LAT), an electrical activity, a topology, a bipolar mapping, a dominant frequency, or an impedance.

5. The method of claim 1, wherein the first set of biometric data is sensed by one or more electrodes.

6. The method of claim 1, wherein the first portion of the body part is one of an entire body part or a subset of the body part.

7. The method of claim 1, wherein the second portion of the body part is determined based on one of a user input or a catheter location.

8. The method of claim 1, further comprising:
   determining, from the first set of biometric data, a third range of values in a third set of biometric data for a third portion of the body part, the third portion of the body part being a subset of the first portion of the body part;
   determining third visual characteristics corresponding to the third range of values;
   providing, for display, a third view comprising the third portion of the body part rendered with the third visual characteristics, the third view superimposed on the first view at a location on the first view corresponding to the third portion of the body part.

9. The method of claim 1, wherein determining first visual characteristics comprises:
   applying a first subset of the first visual characteristics to a low end of the first range; and
   applying a second subset of the first visual characteristic to a high end of the first range.

10. The method of claim 1, further comprising identifying a problem area based on the second view.

11. A system comprising:
a catheter comprising an element configured to sense a first set of biometric data from a first portion of a body part;
a processor configured to:
determine a first range of values in the first set of biometric data;
determine first visual characteristics corresponding to the first range of values;
determine a second range of values in a second set of biometric data from a second portion of the body part, the second portion of the body part comprising a subset of the first portion of the body part and the second set of biometric data being a subset of the first set of biometric data;
determine second visual characteristics corresponding to the second range of values; and
a display configured to:
render a first view comprising the first portion of the body part rendered with the first visual characteristics; and
render a second view comprising the second portion of the body part rendered with the second visual characteristics, the second view superimposed on the first view at a location on the first view corresponding to the second portion of the body part.

12. The system of claim 11, wherein the first visual characteristics and the second visual characteristics are one or more of colors, hues, saturations, patterns, protrusions, textures, and alphanumeric characters.

13. The system of claim 11, wherein the element is configured to sense the first set of biometric data from within a patient's body.

14. The system of claim 11, wherein the first set of biometric data is one of a local activation time (LAT), an electrical activity, a topology, a bipolar mapping, a dominant frequency, or an impedance.

15. The system of claim 11, wherein the element comprises one or more electrodes.

16. The system of claim 11, wherein the first portion of the body part is one of an entire body part and a subset of the body part.

17. The system of claim 11, further comprising an input device configured to receive an indication of the second portion of the body part.

18. The system of claim 11, wherein the display is remotely located from the processor and the display is configured to communicate with the processor over a network.

19. A processor configured to:
receive a first set of biometric data of a first portion of a body part;
determine a first range of values in the first set of biometric data;
determine first visual characteristics corresponding to the first range of values;
determine a second range of values in a second set of biometric data of a second portion of the body part, the second portion of the body part comprising a subset of the first portion of the body part and the second set of biometric data being a subset of the first set of biometric data;
determine second visual characteristics corresponding to the second range of values;
provide, for display, a first view comprising the first portion of the body part rendered with the first visual characteristics; and
provide, for display, a second view comprising the second portion of the body part rendered with the second visual characteristics, the second view superimposed on the first view at a location on the first view corresponding to the second portion of the body part.

20. The processor of claim 19 further configured to provide the first view and the second view to a transmitter.

* * * * *